(12) United States Patent
Ueno

(10) Patent No.: US 8,269,952 B2
(45) Date of Patent: Sep. 18, 2012

(54) SAMPLE ANALYZER INCLUDING A HIGH FREQUENCY CONTROL COMPONENT AND SAMPLE ANALYZING METHOD

(75) Inventor: Kunio Ueno, Hyogo (JP)

(73) Assignee: Sysmex Corporation, Kobe (JP)

( * ) Notice: Subject to any disclaimer, the term of this patent is extended or adjusted under 35 U.S.C. 154(b) by 689 days.

(21) Appl. No.: 12/229,783

(22) Filed: Aug. 27, 2008

(65) Prior Publication Data

US 2009/0059202 A1   Mar. 5, 2009

(30) Foreign Application Priority Data

Aug. 27, 2007   (JP) ................................ 2007-219632

(51) Int. Cl.
   *G01N 33/48* (2006.01)
(52) U.S. Cl. .......................................... 356/39; 356/436
(58) Field of Classification Search .................... 356/39, 356/436; 372/29.011, 29.015, 38.01, 38.02, 372/38.07
   See application file for complete search history.

(56) References Cited

U.S. PATENT DOCUMENTS

| | | | | |
|---|---|---|---|---|
| 4,799,069 | A * | 1/1989 | Sasaki et al. ................... | 347/252 |
| 5,146,464 | A * | 9/1992 | Uemura ....................... | 372/38.07 |
| 5,625,189 | A * | 4/1997 | McCaul et al. ................. | 250/343 |
| 5,930,000 | A * | 7/1999 | Brand ............................ | 356/437 |
| 5,946,333 | A * | 8/1999 | Kappeler ................. | 372/29.022 |
| 6,141,094 | A * | 10/2000 | Tong ............................. | 356/300 |
| 2003/0030783 | A1* | 2/2003 | Roche et al. ..................... | 356/39 |
| 2003/0052250 | A1* | 3/2003 | Taguchi ......................... | 250/205 |
| 2004/0161003 | A1* | 8/2004 | Satou et al. ................ | 372/38.02 |
| 2005/0207943 | A1* | 9/2005 | Puzey ......................... | 422/82.05 |
| 2005/0286392 | A1* | 12/2005 | Kamei .......................... | 369/121 |
| 2006/0045529 | A1* | 3/2006 | Best ............................. | 398/99 |
| 2007/0147451 | A1* | 6/2007 | Sakaguchi ................ | 372/38.02 |
| 2007/0280316 | A1* | 12/2007 | Kitamura ................... | 372/38.02 |

FOREIGN PATENT DOCUMENTS

JP   09-178645   7/1997

* cited by examiner

*Primary Examiner* — Tarifur Chowdhury
*Assistant Examiner* — Michael P LaPage
(74) *Attorney, Agent, or Firm* — Brinks Hofer Gilson & Lione

(57) ABSTRACT

The present invention is to present a sample analyzer capable of automatically stabilizing the laser diode in multi-mode oscillation. A sample analyzer 1 comprises: a laser diode (LD) 501*d* for irradiating a sample with laser light; a photodiode (PD) 501*e* for detecting amount of light emitted from the LD 501*d*; a APC circuit 501*b* for outputting a direct current to be supplied to the LD 501*d* such that the amount of light emitted from the LD 501*d* is maintained at a predetermined amount, based on the amount of light detected by the PD 501*e*; a high frequency oscillation circuit 501*f* for superimposing a high frequency component on the direct current outputted from the APC circuit 501*b*; and a high frequency automatic adjustment circuit 501*c* for controlling amplitude of the high frequency component outputted from the high frequency oscillation circuit 501*f* according to magnitude of the direct current outputted from the APC circuit 501*b* such that the LD 501*d* oscillates in a multi-mode.

17 Claims, 16 Drawing Sheets

RET measurement scattergram

PLT measurement scattergram

SAMPLE ANALYZER INCLUDING A HIGH FREQUENCY CONTROL COMPONENT AND SAMPLE ANALYZING METHOD

RELATED APPLICATIONS

This application claims priority under 35 U.S.C. §119 to Japanese Patent Application No. JP2007-219632 filed Aug. 27, 2007, the entire content of which is hereby incorporated by reference.

FIELD OF THE INVENTION

The present invention relates to a sample analyzer and sample analyzing method for measuring components of biological sample such as blood.

BACKGROUND

A sample analyzer which measures, for example, the size of platelets in blood by the flow cytometry method using a laser diode is disclosed, for example, in U.S. Pat. No. 6,525,807. Such analyzers must reduce the noise of the laser diode in order to perform accurate measurements.

Laser diodes are single mode (oscillation at a single wavelength) when light is continuously emitted. However, the oscillation wavelength of the laser diode changing to another wavelength during single mode oscillation (referred to as a "mode hop" below) can be accomplished by changing the magnitude of the current which is supplied to the laser diode, and changing the temperature of the laser diode. When generating a mode hop, a change occurs in the amount of light output from the laser diode, and the change in the amount of light can be detected as noise. This content is disclosed, for example, in Japanese Laid-Open Patent No. H9-178645, and U.S. Pat. No. 5,946,333. This noise is difficult to distinguish from a detection signal detected when measuring very small particles. It is therefore necessary to suppress the generation of noise caused by mode hopping in order to perform measurements with satisfactory precision.

In the art disclosed in Japanese Laid-Open Patent No. H9-178645 and U.S. Pat. No. 5,946,333, methods are used for maintaining the laser diode in a multi-mode oscillation state (that is, a state in which oscillation occurs at a plurality of wavelengths) by applying a drive current obtained by applying high frequency modulation on a base direct current, so that the laser diode does not settle in a single-mode oscillation state. When such a method is used, the lower limit value (the trough part of a sine wave waveform) of the drive current subjected to high frequency modulation can be reduced to less than the threshold current value of the laser output of the laser diode by manually adjusting the amplitude of the high frequency current. Thus, the laser light output of the laser diode can be repeatedly turned on and off to maintain the laser diode in the multi-mode oscillation state.

In the art disclosed in Japanese Laid-Open Patent No. H9-178645 and U.S. Pat. No. 5,946,333, however, multi-mode oscillation state can not be maintained and mode hopping noise may be generated as the laser diode deteriorates over time.

In consideration of this problem, an object of the present invention is to provide a sample analyzer and sample analyzing method capable of automatically stabilizing the laser diode in multi-mode oscillation.

SUMMARY

A first aspect of the present invention is a sample analyzer, comprising: a laser diode for irradiating a sample with laser light; a light amount detector for detecting amount of light emitted from the laser diode; a direct current output part for outputting a direct current to be supplied to the laser diode such that the amount of light emitted from the laser diode is maintained at a predetermined amount, based on the amount of light detected by the light amount detector; a high frequency superimposing part for superimposing a high frequency component on the direct current outputted from the direct current output part; and a high frequency control part for controlling amplitude of the high frequency component outputted from the high frequency superimposing part according to magnitude of the direct current outputted from the direct current output part such that the laser diode oscillates in a multi-mode.

A second aspect of the present invention is a sample analyzing method for analyzing a sample by irradiating the sample with laser light from a laser diode using a current on which high frequency component is superimposed, comprising: monitoring amount of light emitted from the laser diode; controlling magnitude of a direct current to be supplied to the laser diode such that the amount of light emitted from the laser diode is maintained at a predetermined amount, based on the amount of light monitored in the monitoring step; and controlling amplitude of the high frequency component superimposed on the direct current according to the magnitude of the direct current supplied to the laser diode in the magnitude controlling step such that the laser diode oscillates in a multi-mode.

DETAILED DESCRIPTION OF THE EMBODIMENT

[General Structure of the Sample Analyzer]

The general structure of an embodiment of a sample analyzer 1 of the present invention is described below referring to FIG. 1.

Although the sample analyzer 1 is configured as a multi-item automatic blood cell analyzer which performs blood analysis, the following description examines only the measurement of white blood cells, reticulocytes, and platelets in blood.

Figure 1:
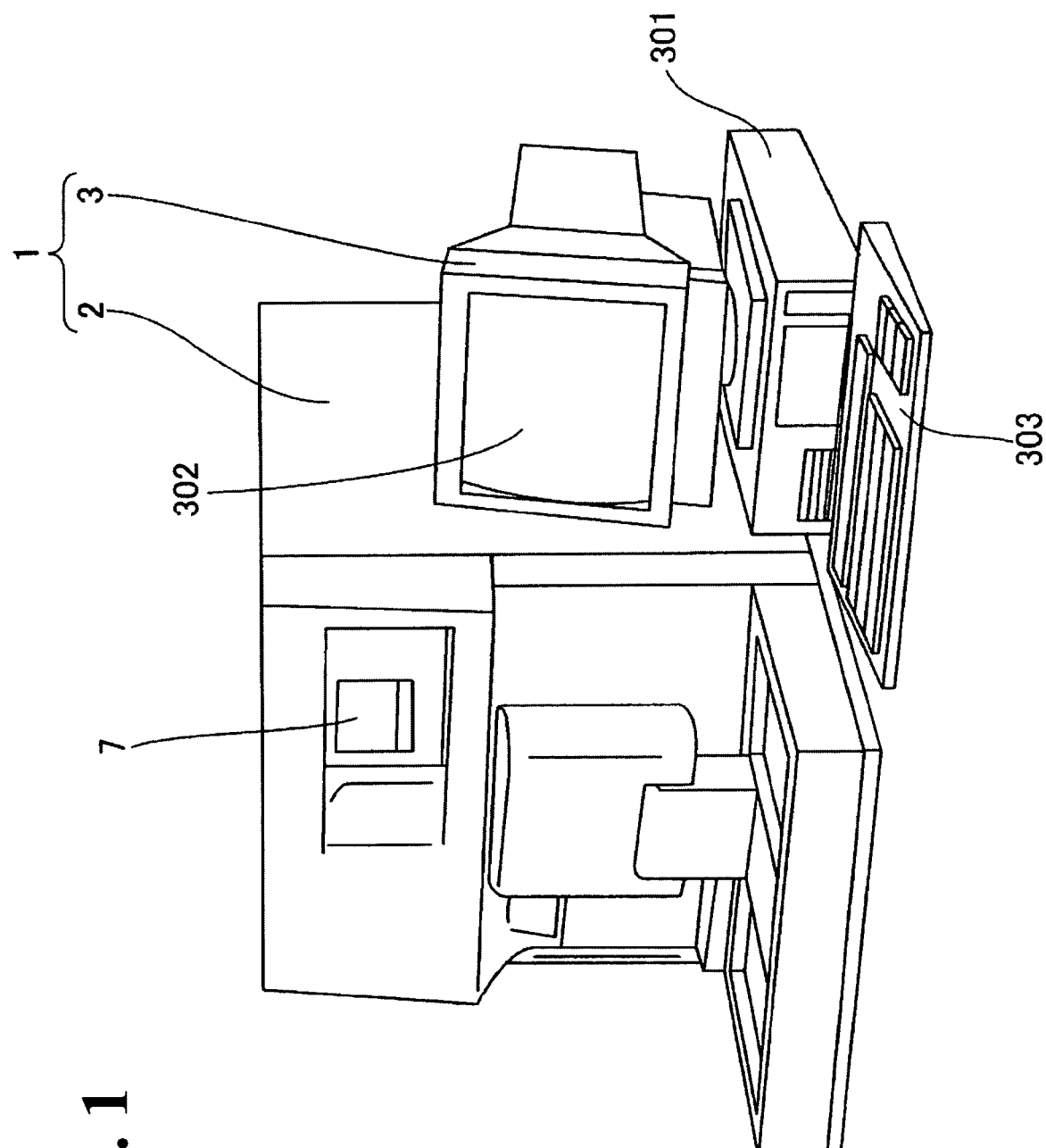
FIG. 1 is a perspective view showing an embodiment of the sample analyzer of the present invention.

As shown in FIG. 1, the sample analyzer 1 is configured by a measuring section 2 which has the function of measuring a biological sample of blood, and a data processing section 3 which functions as an analyzing means for analyzing the measurement data received from the measuring section 2 and obtaining analysis results. The measuring section 2 is configured to measure the white blood cells, reticulocytes, and platelets in blood using flow cytometry. Flow cytometry is a method in which a sample flow is formed which contains the measurement sample, and the particles (blood cells) in the measurement sample are measured by irradiating the sample flow with laser light and detecting the forward scattered light, side scattered light, and side fluorescent light emitted from the particles (blood cells).

[Measuring Section]

Figure 2:
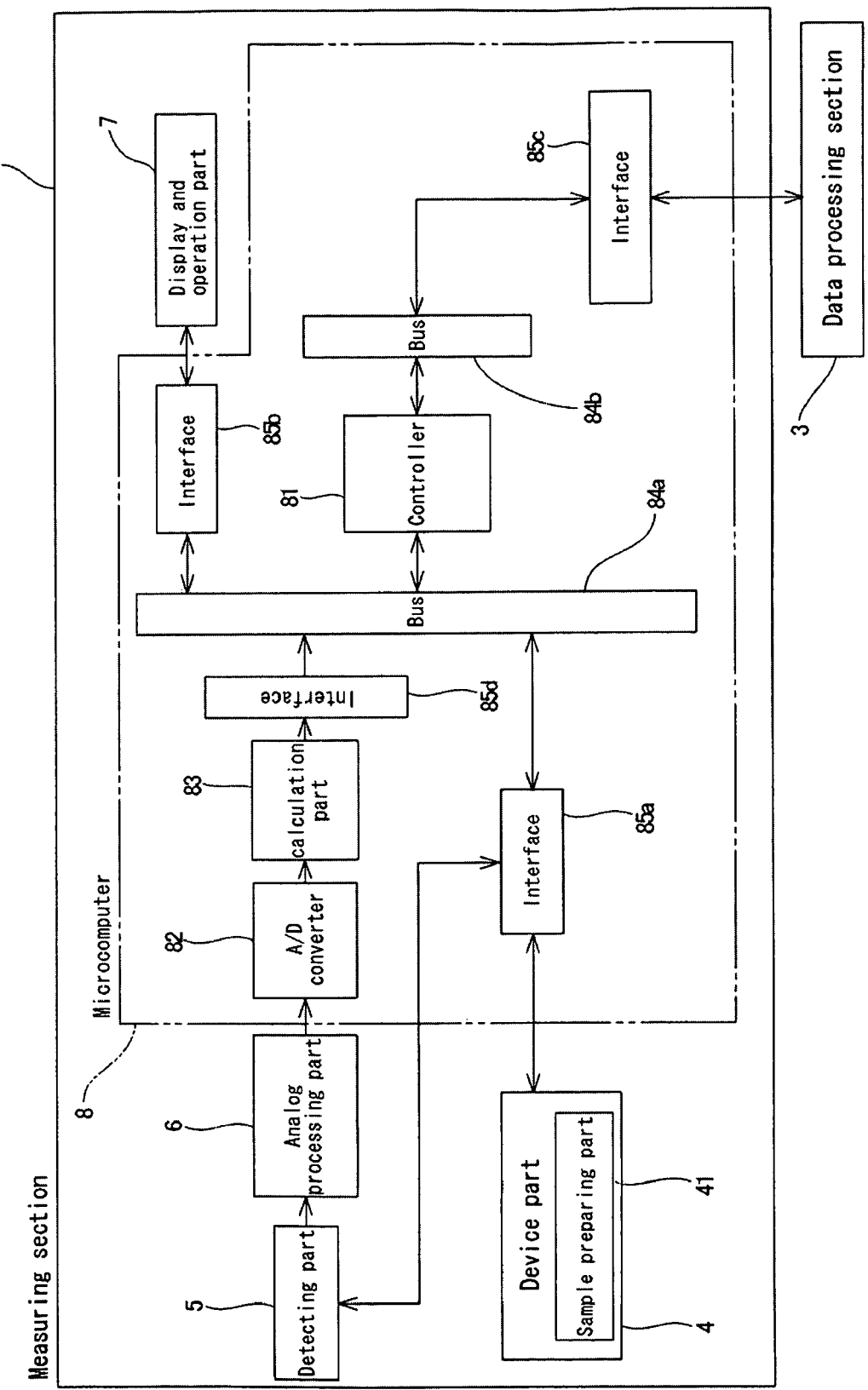
FIG. 2 is a block diagram showing the structure of the measuring section of the sample analyzer of FIG. 1.

As shown in FIG. 2, the measuring section 2 is provided with a device part 4, a detecting part 5 which detects the light from the blood cells in the measurement sample, an analog processing part 6 which processes the output of the detecting part 5, a display and operation part 7, and a microcomputer 8 which controls the measuring section 2.

The microcomputer 8 includes a controller 81 which has a control processor, and a memory for operating the control processor, an A/D converter 82 which converts the signals output from the analog processing part 6 to digital signals, and calculation part 83 which performs predetermined processing on the digital signals output from the A/D converter 82, as shown in FIG. 2. The controller 81 has the function of controlling the device part 4 and the detecting part 5 through a bus 84a and an interface 85a. The controller 81 is also connected to the display and operation part 7 through the bus 84a and an interface 85b, and is connected to the data processing section 3 through a bus 84b and an interface 85c. The calculation part 83 has the function of outputting calculation results to the controller 81 through an interface 85d and the bus 84a. The controller 81 also has the function of transmitting the calculation results (measurement data) to the data processing section 3.

Figure 3:
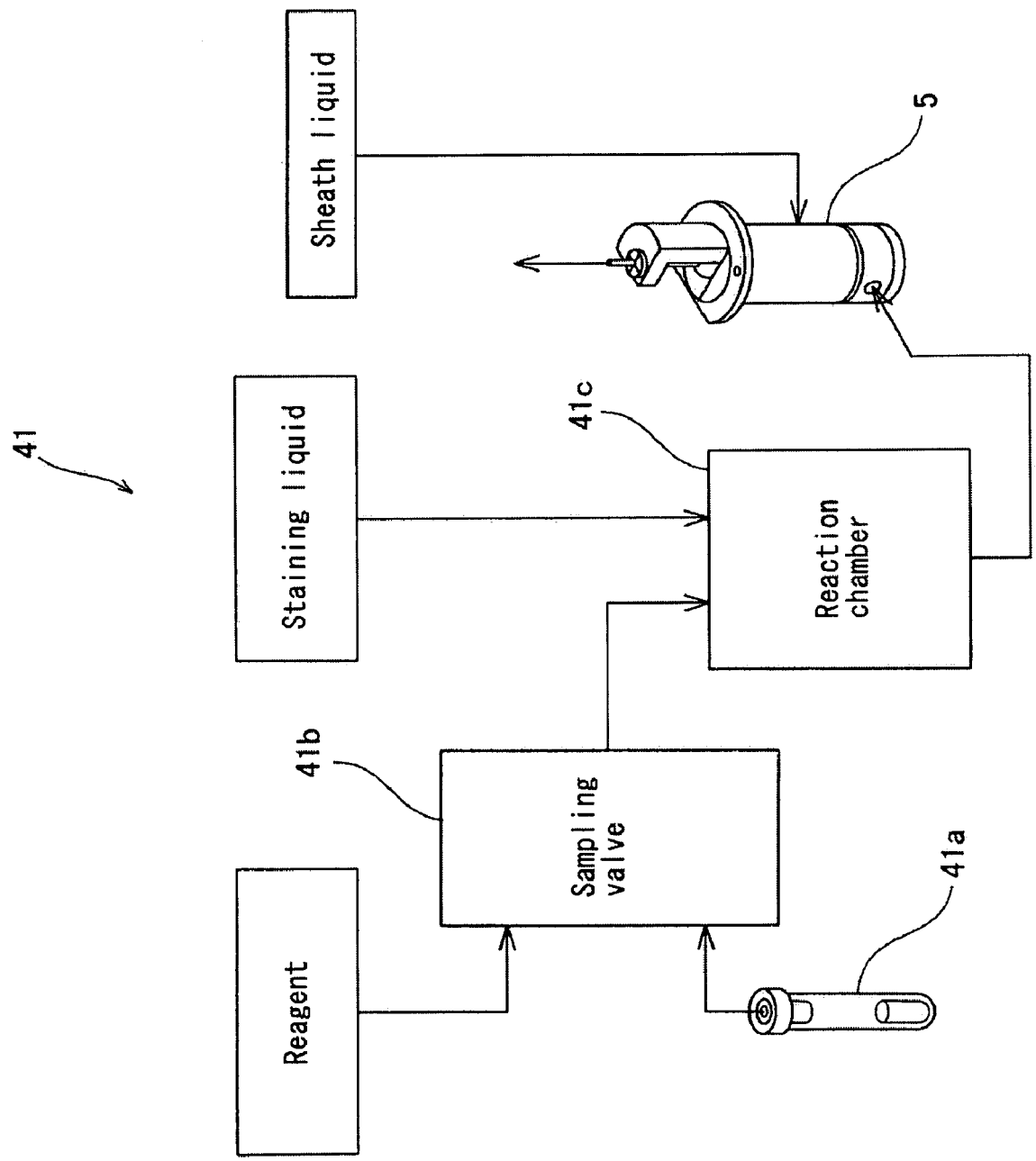
FIG. 3 illustrates the sample preparing section of the sample analyzer of FIG. 1.

The device part 4 is provided with a sample preparing section 41 which prepares a measurement sample from reagent and blood. The sample preparing section 41 is provided to prepare a white blood cell measurement sample, reticulocyte measurement sample, and platelet measurement sample. The sample preparing section 41 includes a blood collection tube 41a which is filled with a predetermined amount of blood, a sampling valve 41b which aspirates the blood, and a reaction chamber 41c, as shown in FIG. 3. The blood collection tube 41a is replaceable, and configured to allow blood to be exchanged. The sampling valve 41b has the function of measuring a predetermined fixed amount of blood within the blood collection tube 41a which has been aspirated by an aspirating pipette (not shown in the drawing).

The sampling valve 41b is configured to be capable of mixing a predetermined reagent in the aspirated blood. That is, the sampling valve 41b is configured to be capable of generating a dilute sample in which a predetermined amount of reagent is mixed in a predetermined amount of blood. The reaction chamber 41c is configured so that a predetermined staining liquid is further mixed in the dilute sample which is supplied from the sampling valve 41b, and reacted for a predetermined time. The sample preparing section 41 has the function of preparing a measurement sample of stained white blood cells together with hemolyzed red blood cells as a white blood cell measurement sample. The sample preparing section 41 also has the function of preparing a measurement sample of stained reticulocytes as a reticulocyte measurement sample, and preparing a measurement sample of stained platelets as a platelet measurement sample.

The device part 4 (FIG. 2) is configured to supply the white blood cell measurement sample and a sheath liquid together from the sample preparing section 41 to a sheath flow cell 503 (FIG. 4) which is described later when the white blood cell classification measurement (hereinafter referred to as "DIFF measurement") mode is set. The device part 4 is further configured to supply the reticulocyte measurement sample together with a sheath liquid from the sample preparing section 41 to the sheath flow cell 503 when the reticulocyte measurement (hereinafter referred to as "RET measurement") mode is set. The device part 4 is further configured to supply the platelet measurement sample together with a sheath liquid from the sample preparing section 41 to the sheath flow cell 503 when the platelet measurement (hereinafter referred to as "PLT measurement") mode is set.

Figure 4:
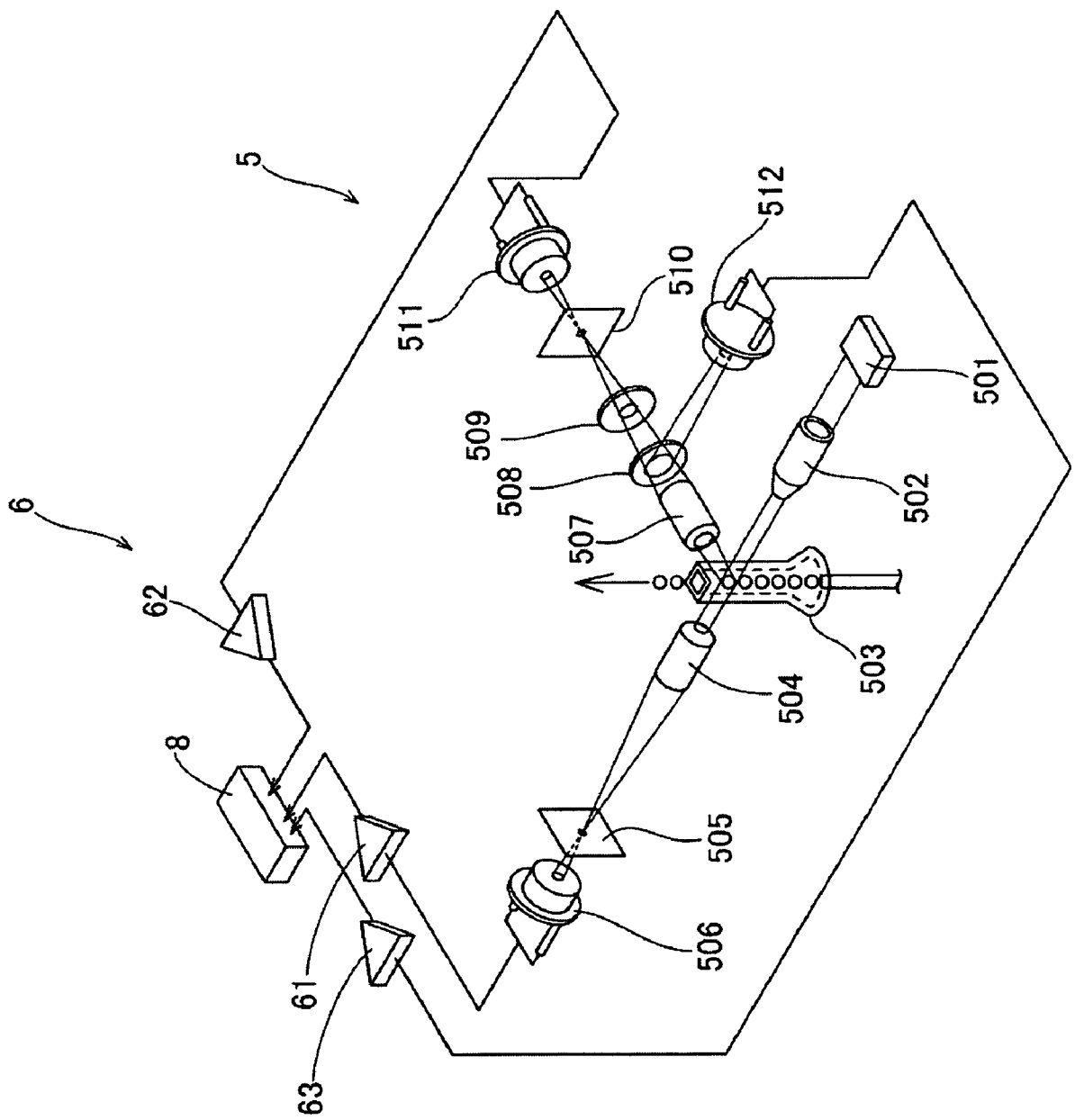
FIG. 4 briefly shows the detecting section of the sample analyzer of FIG. 1.

As shown in FIG. 4, the detecting part 5 includes a light emitting part 501 which emits laser light; an irradiation lens unit 502; a sheath flow cell 503 which is irradiated with laser light; a collective lens 504 which is disposed on a line extending in the direction of travel of the laser light emitted from the light emitting part 501; a pinhole 505 and PD (photodiode) 506; (a beamsplitter disposed between the sheath flow cell 503 and the collective lens 504 but not shown in the drawing); a collective lens 507 which is disposed in a direction which intersects the direction of travel of the laser light emitted from the light emitting part 501; a dichroic mirror 508; an optical filter 509; a pinhole 510 and APD (avalanche photodiode) 511; and a PD 512 which is disposed at the side of the dichroic mirror 508.

The light emitting part 501 is provided to emit light on the sample flow which contains the measurement sample passing through the interior of the sheath flow cell 503. The irradiation lens unit 502 is provided to render the emitted light from the light emitting part 501 into parallel rays. The PD 506 is provided to receive the forward scattered light emitted from the sheath flow cell 503. Information related to the size of the particles (blood cells) in the measurement sample can be obtained from the forward scattered light emitted from the sheath flow cell 503.

The dichroic mirror 508 is provided to separate the side scattered light and the side fluorescent light emitted from the sheath flow cell 503. Specifically, the dichroic mirror 508 is provided to direct the side scattered light emitted from the sheath flow cell 503 into the PD 512, and to direct the side fluorescent light emitted from the sheath flow cell 503 into the APD 511. The PD 512 is provided to receive the side scattered light. Internal information such as the size of the nucleus and the like of the particles (blood cells) in the measurement sample can be obtained from the side scattered light emitted from the sheath flow cell 503. The APD 511 is provided to receive the side fluorescent light. Information related to the degree of staining of the particles (blood cells) in the measurement sample can be obtained from the side fluorescent light emitted from the sheath flow cell 503. The PD 506, PD 512, and APD 511 respectively functions of converting the optical signals of the received light to electrical signals.

In the present embodiment, the light emitting part 501 is configured so that light is emitted with an output of 3.4 mW when the DIFF measurement mode is set. The light emitting part 501 is also configured so that light is emitted with an output of 6 mW when the RET measurement mode is set. The light emitting part 501 is also configured so that light is emitted with an output of 10 mW when the PLT measurement mode is set.

[Data Processing Section]

Figure 5:
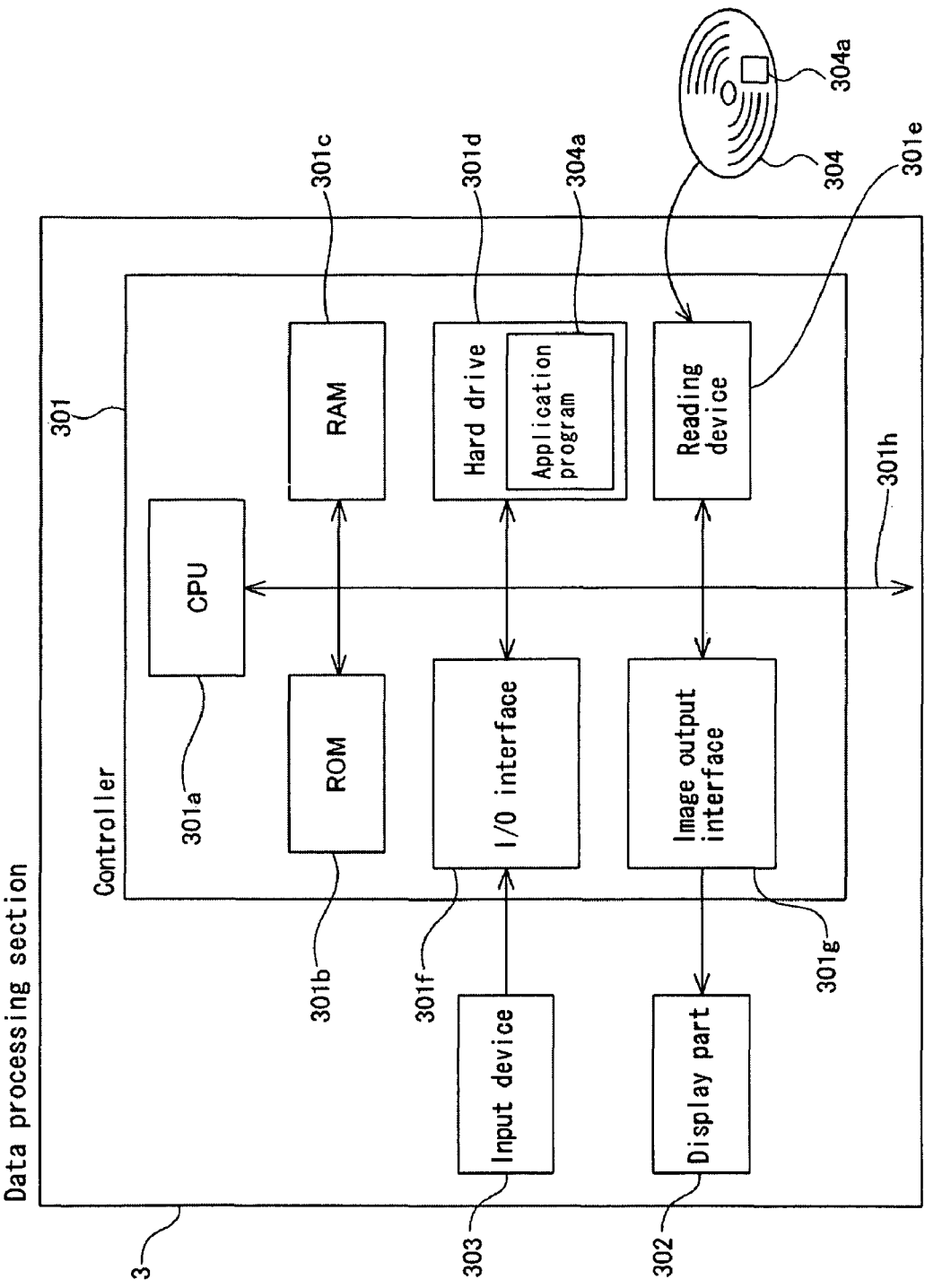
FIG. 5 is a block diagram showing the structure of the data processing section of the sample analyzer of FIG. 1.

The data processing section 3 is configured by a personal computer (PC), and has the function of analyzing the measurement data of the measuring section 2 and displaying the analysis results, as shown in FIG. 1. The data processing section 3 includes a controller 301, a display part 302, and an input device 303. The controller 301 has the function of transmitting the measurement start signal, which contains the measurement mode information, and the shutdown signal to the measuring section 2. The controller 301 is configured by a CPU 301*a*, a ROM 301*b*, a RAM 301*c*, a hard disk 301*d*, a reading device 301*e*, an input/output interface 301*f*, and an image output interface 301*g*, as shown in FIG. 5. The CPU 301*a*, ROM 301*b*, RAM 301*c*, hard disk 301*d*, reading device 301*e*, input/output interface 301*f*, and image output interface 301*g* are connected by a bus 301*h*.

The CPU 110*a* is provided to execute computer programs stored in the ROM 301*b*, and computer programs loaded in the RAM 301*c*. The ROM 301*b* is configured by a mask ROM, PROM, EPROM, EEPROM or the like, and stores computer programs executed by the CPU 301*a* and data and the like used in conjunction therewith.

The RAM 301*c* is configured by SRAM, DRAM or the like. The RAM 301*c* is used when reading the computer programs recorded in the ROM 301*b* and on the hard drive 301*d*. The RAM 301*c* is also used as a work area of the CPU 301*a* when the computer programs are being executed.

The hard drive 301*d* contains various installed computer programs to be executed by the CPU 301*a* such as an operating system and application program and the like, as well as data used in the execution of these computer programs. Also installed on the hard disk 301*d* is the application program 304*a* which is described later.

The reading device 301*e* is configured by a floppy disk drive, CD-ROM drive, DVD-ROM drive or the like, and is capable of reading the computer programs and data stored on a portable recording medium 304. The portable recording medium 304 stores the application program 304*a* which realizes predetermined functions on a computer, and the application 304*a* is read from the portable recording medium 304 by the computer which can install the application program 304*a* on the hard disk 304*d*.

The application program 304*a* is not only provided via the portable recording medium 304 inasmuch as the application program 304*a* may also be provided from an external device which is connected to the computer over an electric communication line so as to be capable of communication via this electric communication line (whether wire line or wireless). For example, when the application program 304*a* is stored on the hard disk of a server computer on the Internet, the data processing section 3 accesses the server computer and downloads the application program 304*a*, which is then installed on the hard disk 304*d*.

An operating system which provides a graphical user interface, such as Windows (registered trademark), a product of Microsoft Corporation, USA, or the like is installed on the hard disk 304*d*. In the following description, the application program 304*a* of the present embodiment operates on this operating system in the following description.

The Input/output interface 301*f* is configured, for example, by a serial interface such as a USB, IEEE1394, RS232C or the like, parallel interface such as SCSI, IDE, IEEE1284 or the like, or an analog interface such as a D/A converter, A/D converter or the like. The input/output interface 301*f* is connected to the input device 303 which is configured by a keyboard and mouse, and a user can input data through the input/output interface 301*f* to the data processing section 3 by using the input device 303. The input/output device 303 also has the function of receiving the measurement mode. Specifically, the input device 303 has the function of respectively receiving the DIFF measurement, RET measurement, and PLT measurement mode instruction for predetermined blood.

The image output interface 301*g* is connected to the display part 302 which is configured by an LCD, CRT or the like, so that image signals corresponding to the image data received from the CPU 301*a* can be output to the display part 302. The display part 302 displays an image (screen) according to the input image signal.

[Light Emitting Part in the Detecting Part of the Measuring Section]

Figure 6:
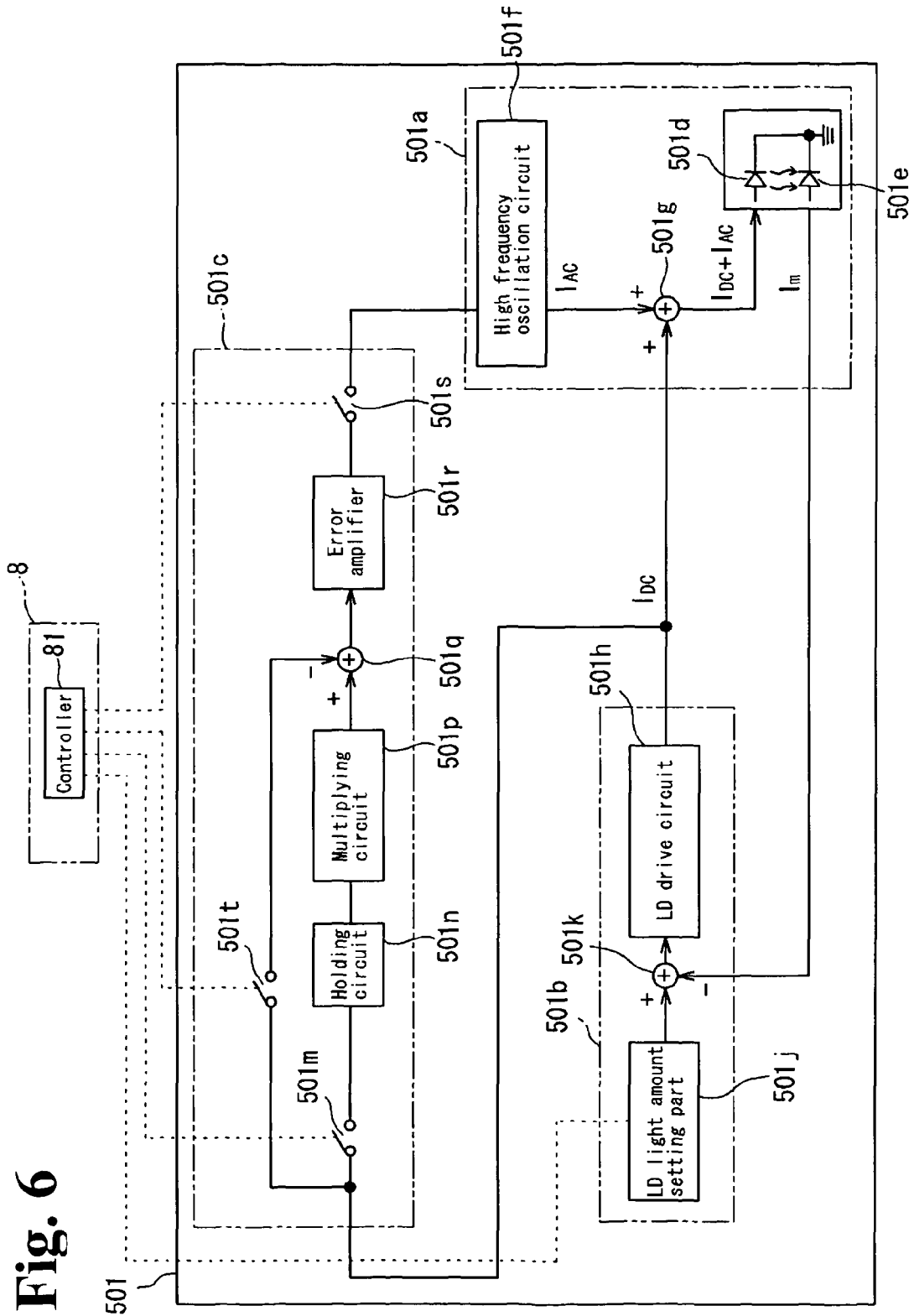
FIG. 6 is a block diagram showing the structure of light emitting section of the sample analyzer of FIG. 1.

The light emitting part 501 in the detecting part 5 of the measuring section 2 includes light emitting part body 501*a*, APC (automatic power circuit) circuit 501*b* which controls the amount of light emitted from the light emitting body 501*a*, and a high frequency automatic adjustment circuit 501*c*, as shown in FIG. 6.

In the present embodiment, the light emitting part body 501*a* has an LD (laser diode) 501*d* which emits light on the sample flow of the sheath flow cell 503, a PD (photodiode) 501*e* which receives the light emitted from the LD 501*d*, a high frequency oscillation circuit 501*f*, and an adder 501*g*. The PD 501*e* has the function of converting the received optical signal to an electrical signal. The adder 501*g* adds a direct current $I_{DC}$ supplied from the APC circuit 501*b* to a high frequency current $I_{AC}$ (the frequency is, for example, 500 MHz) output from the high frequency oscillation circuit 501*f*. The LD 501*d* can be set to multi-mode oscillation of several oscillation wavelengths by supplying a drive current ($I_{DC}$+$I_{AC}$) configured by the high frequency current $I_{AC}$ superimposed on the direct current $I_{DC}$ to the LD 501*d*. The APC circuit 501*b* is a direct current drive circuit which outputs a direct current to be supplied to the LD 501*d* so as to maintain the amount of light emitted by the LD 501*d* at a predetermined amount based on the amount of light detected by the PD 501*e*. The high frequency oscillation circuit 501*f* and the adder 501*g* configure a high frequency superimposing circuit which outputs a high frequency current superimposed on a direct current output from the APC circuit 501*b*.

In the present embodiment, the APC circuit 501*b* is provided with an LD drive circuit 501*h* which supplies the direct current $I_{DC}$ to the LD 501*d*, an LD light amount setting part 501*j* which sets the LD light amount, and a comparator 501*k* that applies an output, which corresponds to the difference between the output of the LD light amount setting part 501j and a monitor current Im which represents the amount of light received by the PD 501e, to the LD drive circuit 501h. The LD drive circuit 501h is therefore controlled so that the amount of light emitted from the LD 501d approaches the amount of light set by the LD light amount setting part 501j.

A control signal is supplied from the controller 81 to the LD light amount setting part 501j to set the amount of light. Specifically, the amount of light is set so that the output of the LD 501d is one of the values below.

DIFF measurement mode: 3.4 mW
RET measurement mode: 6 mW
PLT measurement mode: 10 mW The LD 501d is set to the off state when these measurements are not being performed.

The high frequency automatic adjustment circuit 501c, which is a high frequency current control means, is provided with a switch 501m, a holding circuit 501n for storing input signals, a multiplying circuit 501p for multiplying by multiplying factor of 0.95 as a predetermined value, a comparator 501q, an error amplifier 501r, a switch 501s, and a switch 501t, which are connected as shown in the drawing. The switches 501m, 501s, 501t are turned on and off by instructions from the controller 81 (details to follow). The signal input to the high frequency automatic adjustment circuit 501c is a voltage signal equivalent to the direct current $I_{DC}$, and the high frequency bias output from the high frequency automatic adjustment circuit 501c is an instruction value which determines the amplitude of the high frequency current.

Figure 15:
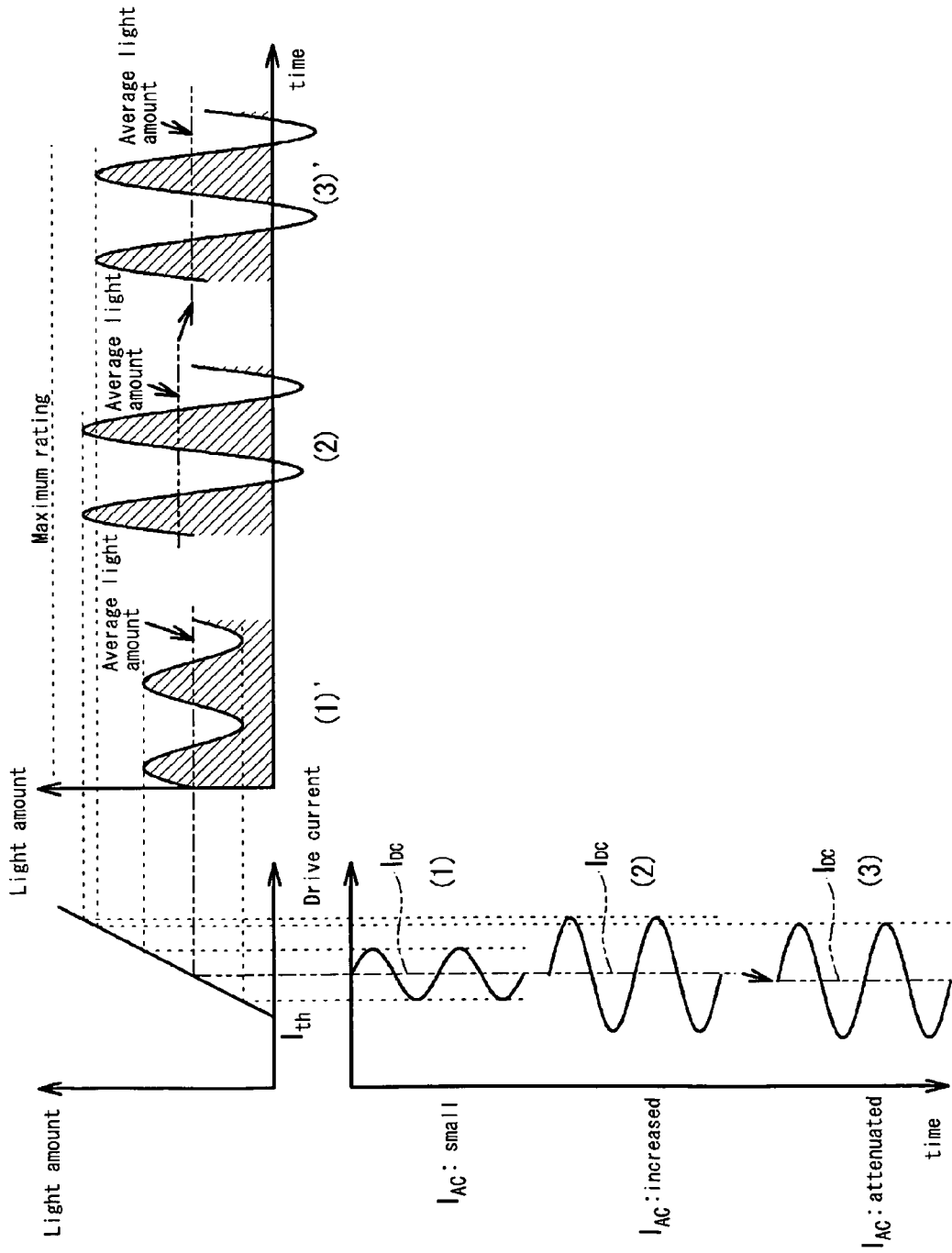
FIG. 15 illustrates the relationship between the drive current ($I_{DC}+I_{AC}$) and the switching of the laser diode (LD) by the high frequency bias.

FIG. 15 shows the relationship between the drive current ($I_{DC}+I_{AC}$) and the switching of the LD 501d by the high frequency bias. The top left is a graph which shows the relationship between the drive current and the amount of light; when the drive current is equal to or greater than a threshold value $I_{th}$, the amount of light is proportional to the drive current. The bottom left is a graph which shows the change in the drive current; the change this produces in the amount of light is shown in the graph on the right side. In the drawing, (1) indicates the waveform of a drive current in which a relatively small $I_{AC}$ is superimposed on the $I_{DC}$; in this case the minimum value of the drive current is equal to or greater than the threshold value $I_{th}$. The amount of light at this time modulates as shown by the shaded area indicates by (1)'; the average amount of light does not vary with the drive time and only $I_{DC}$.

Then, the $I_{AC}$ is gradually increased and when the amplitude shown in (2) is reached, the minimum value of $I_{DC}+I_{AC}$ falls below the threshold value $I_{th}$, and the amount of light modulates as indicated in (2)'. In this case, the LD 501d attains a multi-mode oscillation state by the generation of the period during which the LD is turned off. Since the switching produces waveform distortion, the average amount of light increases from that of $I_{DC}$ alone. When the amount of light increases, the APC circuit 501b operates to maintain a constant amount of light by increasing the monitor current $I_m$ of FIG. 6. As a result, the $I_{DC}$ decreases as shown in (3), and the average amount of light is identical to (1)' as shown in (3)'. The multiplying factor of the multiplying circuit 501p in the high frequency automatic adjustment circuit 501c is set at 0.95 and the value of the $I_{DC}$ after the decrease is controlled to be approximately 95% of the initial value to cause the LD 501d to reliably hold the multi-mode oscillation state. Insofar as the LD 501d reliably holds the multi-mode oscillation state, the multiplying factor of the multiplying circuit 501p is not specifically limited, and a factor of 0.96, 0.97 or the like may also be used.

[Sample Analysis Operation]

Figure 7:
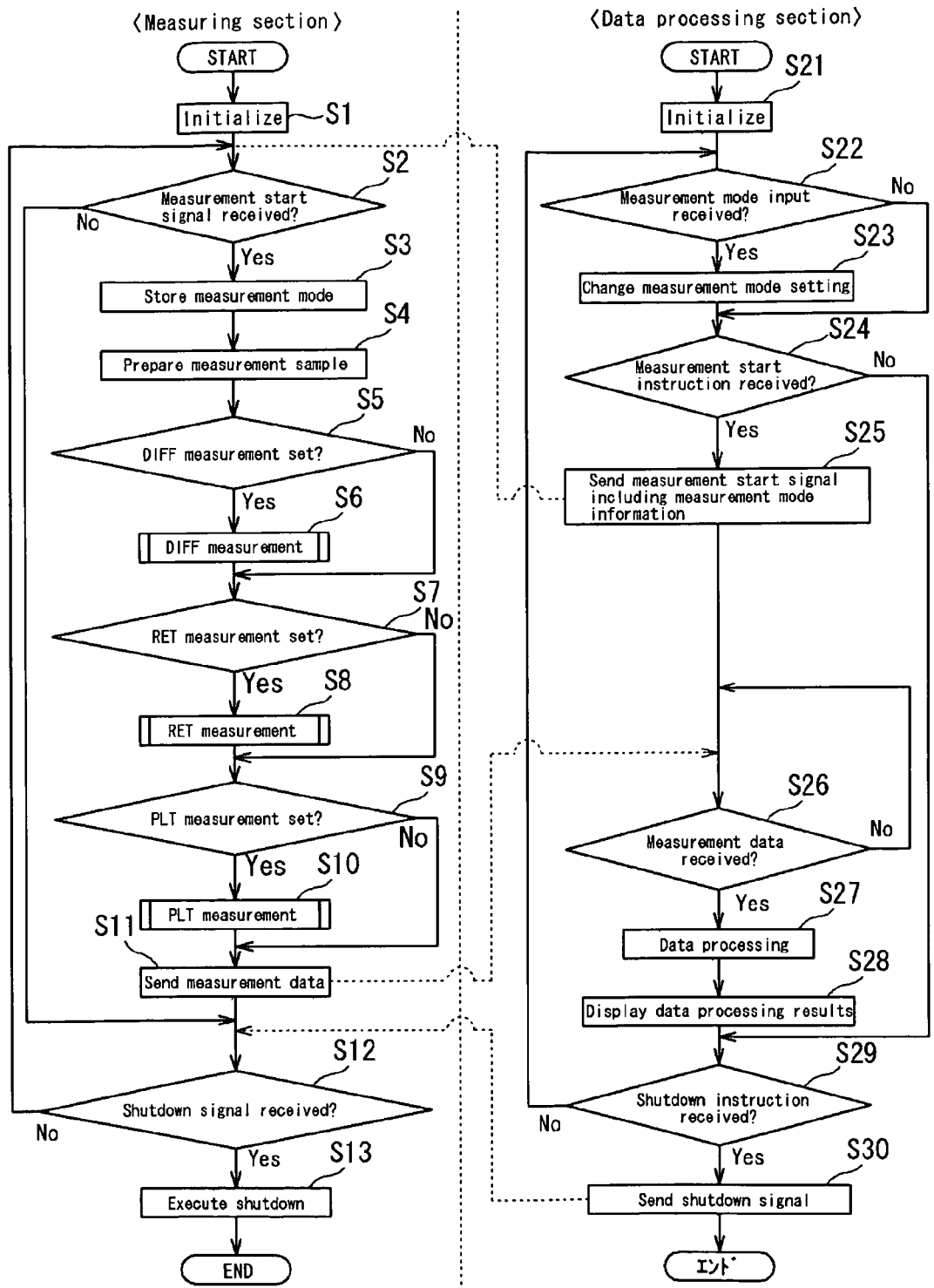
FIG. 7 is a flow chart illustrating the analysis operation of the embodiment of the sample analyzer of the present invention.

FIG. 7 is a flow chart illustrating the blood analysis operation of the embodiment of the sample analyzer of the present invention. The blood analysis operation of the sample analyzer 1 of an embodiment of the present invention is described below with reference to FIG. 7 and related drawings.

When a main switch, which is provided on the measuring section 2 (FIG. 2) but not shown in the drawing, is first turned on in step S1 of FIG. 7, the controller 81 (FIG. 2) is initialized, and an operation check is performed for each part of the measuring section 2. Thereafter, the operation advances to step S2.

In step S21 of FIG. 7, the controller 301 (FIG. 5) in the data processing section 3 is initialized (program initialization). The controller 301 then displays the menu screen (not shown in the drawing) on the display part 302 (FIGS. 1 and 5). A user selects whether or not to set the DIFF measurement mode, RET measurement mode, and PLT measurement mode on the menu screen, and the measurement start instruction and shutdown instruction are received from the user via the menu screen.

In step S22 the controller 301 determines whether or not measurement mode input has been received, and measurement mode input has been received the measurement mode setting is changed in step S23. Specifically, the received measurement mode is set by the input device 303 (FIGS. 1, 5). The operation advances to step S24 when measurement mode input has not been received.

In step S24 the controller 301 determines whether or not a measurement start instruction has been received, and the operation advances to step S25 when a measurement start instruction has been received. If a measurement start instruction has not been received, the operation advances to step S29. In step S29 the controller 301 transmits a measurement start signal which includes the measurement mode information to the measuring section 2. Thereafter, the operation advances to step S26.

Furthermore, when the controller 81 (FIG. 2) determines whether or not a measurement start signal has been received from the data processing section 3 (FIGS. 1, 2) in step S2 and determines that a measurement start signal has been received, the operation then advances to step S3. When a measurement start signal has not been received, the operation advances to step S12.

In step S3 the controller 81 stores the measurement mode within the measurement start information. Specifically, whether or not the DIFF measurement mode, RET measurement mode, or PLT measurement mode is set is stored. A measurement sample for the set measurement mode is prepared in step S4. Specifically, a dilute sample, which is a mixture of a predetermined amount of reagent mixed with a predetermined amount of blood, is prepared by supplying the predetermined reagent to the sampling valve 41b (FIG. 3). The dilute sample is supplied to the reaction chamber 41c (FIG. 3), and a predetermined amount of staining liquid is supplied to the reaction chamber 41c. As a result, the dilute sample is mixed with the staining liquid and reacted for a predetermined time.

In step S5, the controller 81 then determines whether or not the DIFF measurement mode is set; when the DIFF measurement mode is set, the operation advances to step S6 and DIFF measurement is performed. The DIFF measurement operation is described in detail later. When the DIFF measurement mode is not set, the operation advances to step S7.

In step S7 the controller 81 determines whether or not the RET measurement mode is set; when the RET measurement mode is set the operation advances to step S8 and RET measurement is performed. The RET measurement operation is described in detail later. When the RET measurement mode is not set, the operation advances to step S9.

In step S9 the controller 81 determines whether or not the PLT measurement mode is set; when the PLT measurement mode is set, the operation advances to step S10 and PLT measurement is performed. The PLT measurement operation is described in detail later. When the PLT measurement mode is not set, the operation advances to step S11.

In step S11 the controller 81 transmits the measurement results (measurement data) of the set measurement mode to the data processing section 3 through the bus 84*b* (FIG. 3) and the interface 85*c* (FIG. 3). Thereafter, the operation advances to step S12.

Furthermore, in step S26 the controller 301 in the data processing section 3 determines whether or not measurement results (measurement data) have been received from the measuring section 2; when the measurement data have been received, the operation advances to step S27. When the measurement data have not been received, the process of step S26 is repeated until it is determined that measurement data have been received.

In step S27 the CPU 301*a* (FIG. 5) stores the received measurement data on the hard drive 301*d* (FIG. 5). The CPU 301*a* thereafter stores the measurement data in the RAM 301*c* (FIG. 5). Then the CPU 301*a* analyzes the measurement data read from the RAM 301*c*. In step S28 the CPU 301*a* outputs the analyzed measurement data to the display part 302 through the image output interface 301*g*.

Figure 8:
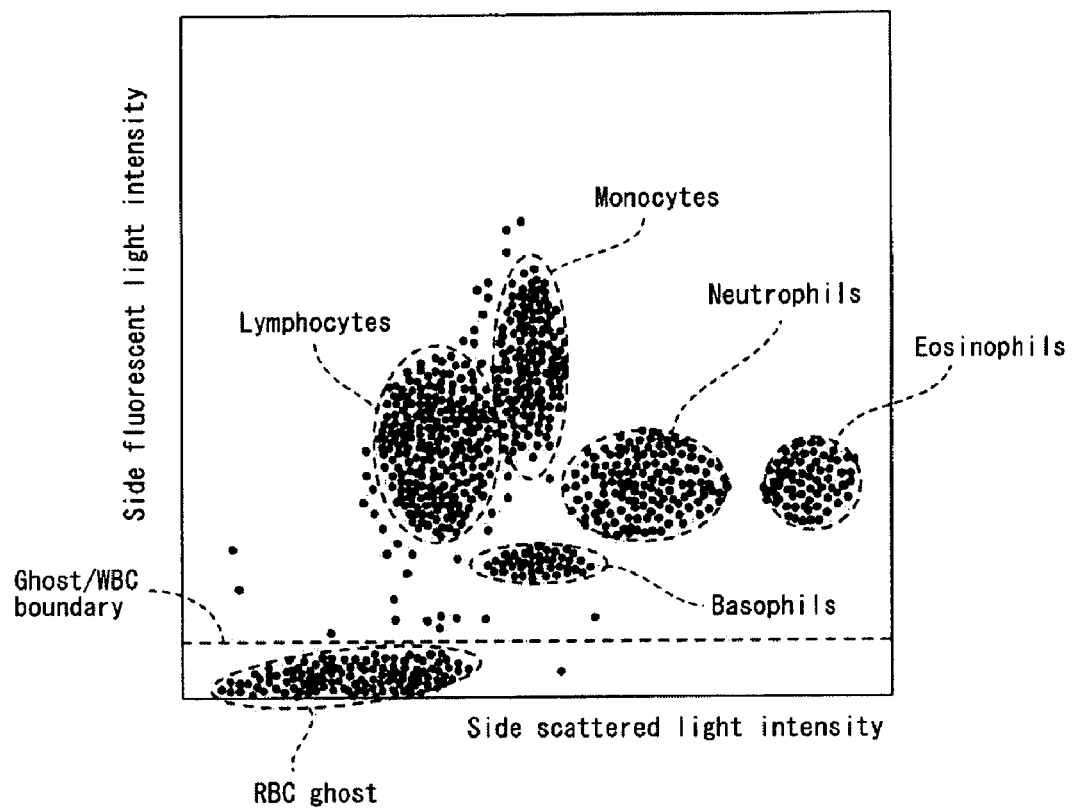
FIG. 8 is a scattergram showing the results of the DIFF measurement performed by the embodiment of the sample analyzer of the present invention.
Figure 9:
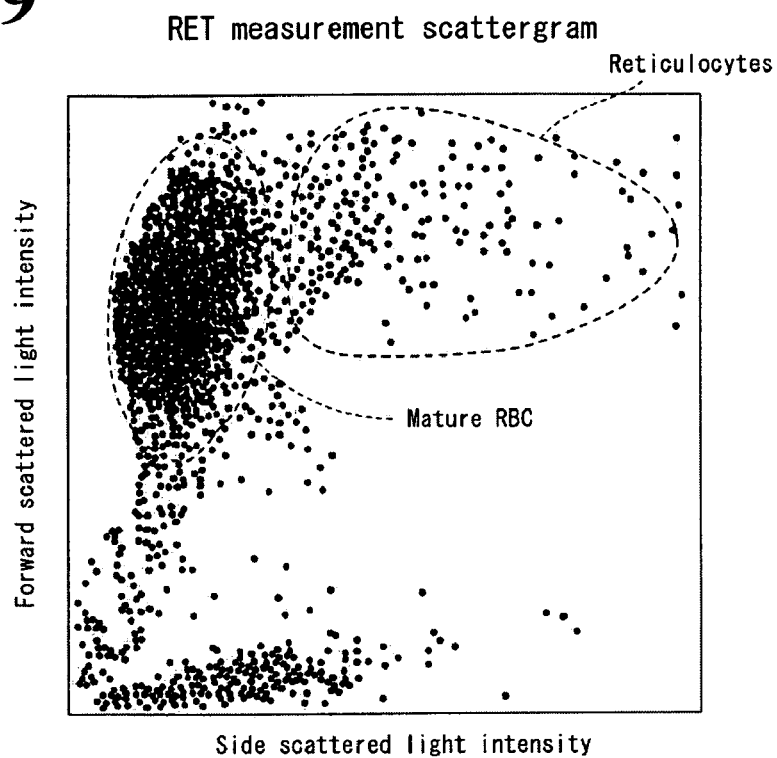
FIG. 9 is a scattergram showing the results of the RET measurement performed by the embodiment of the sample analyzer of the present invention.
Figure 10:
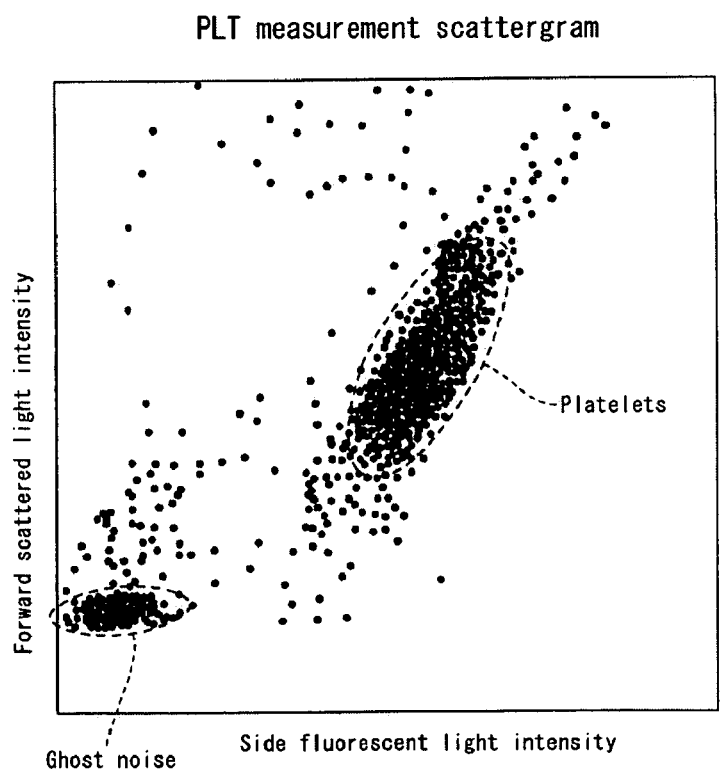
FIG. 10 is a scattergram showing the results of the PLT measurement performed by the embodiment of the sample analyzer of the present invention.

Specifically, when the DIFF measurement is performed in step S6, the lymphocytes, monocytes, neutrophils, basophils, and eosinophils in the blood are classified and counted in the analysis process, and thereafter a scattergram is displayed, such as that shown in FIG. 8. When the RET measurement is performed in step S8, the reticulocytes in the blood are classified and counted in an analysis process and thereafter a scattergram is displayed, such as that shown in FIG. 9. When the PLT measurement is performed in step S10, the platelets in the blood are classified and counted in an analysis process and thereafter a scattergram is displayed, such as that shown in FIG. 10. The measurement results which include the amount of light emitted from the analysis sample in each measurement mode can be visually recognized by the operator via the displayed scattergram, such as those shown in FIGS. 8 through 10.

In step S29 the controller 301 determines whether or not a shutdown instruction has been received; when a shutdown instruction has been received, a shutdown signal is transmitted to the measuring section 2 in step S30 and the process ends thereafter. When a shutdown instruction has not been received, the operation returns to step S22.

In step S12 the controller 81 of the measuring section 2 determines whether or not a shutdown signal has been received from the data processing section 3; when a shutdown signal has been received, the measuring section 2 is shut down in step S13 and the process ends thereafter. When a shutdown signal has not been received, the operation returns to step S2.

[DIFF Measurement]

Figure 11:
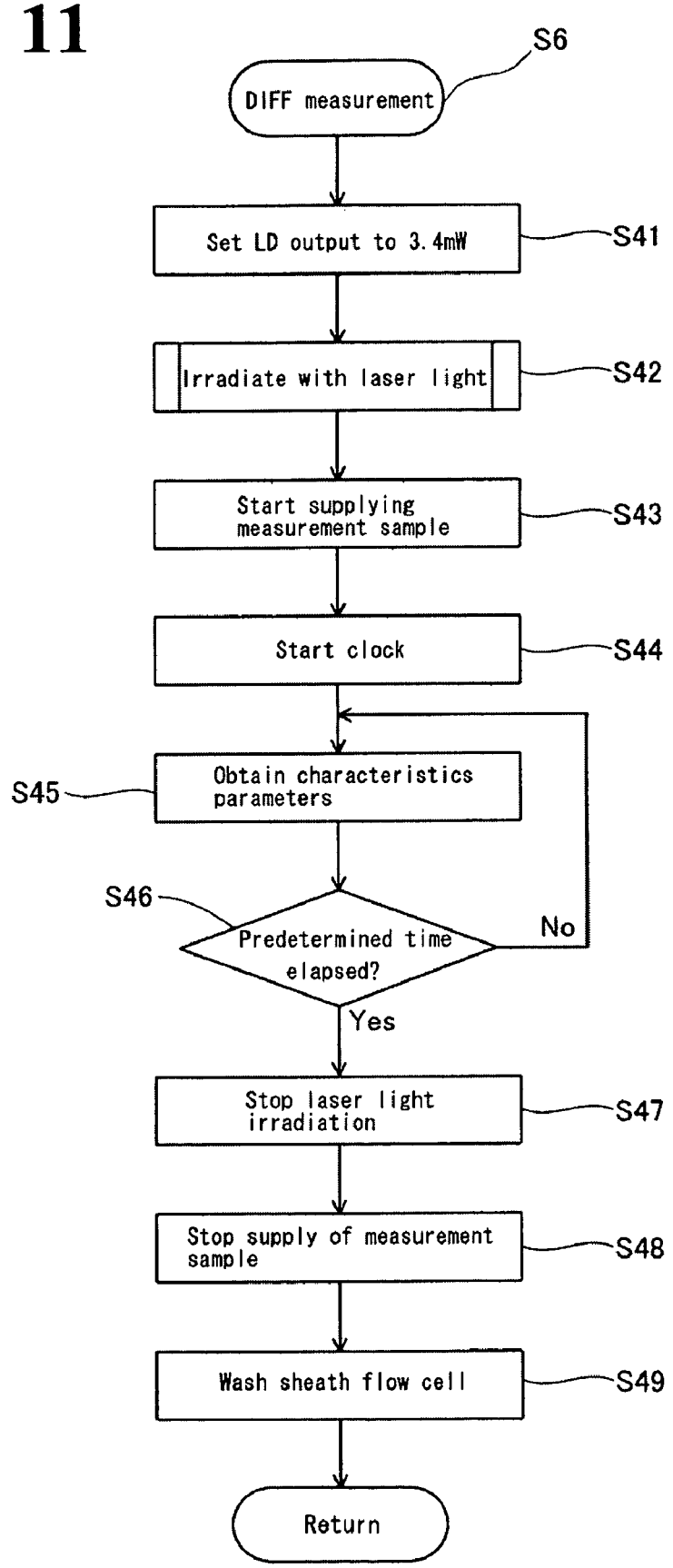
FIG. 11 is a flow chart illustrating the DIFF measurement operation of the embodiment of the sample analyzer of the present invention.

FIG. 11 is a flow chart illustrating the DIFF measurement operation of the embodiment of the sample analyzer of the present invention. Details of the DIFF measurement of step S6 shown in FIG. 7 are described below with reference to FIG. 11 and related drawings.

The controller 81 (FIG. 2) sets the output of the LD 501*d* (FIG. 6) at 3.5 mW in step S41 in FIG. 11. In step S42 laser light irradiates the sheath flow cell 503 (FIG. 4). Specifically, a control signal is supplied from the controller 81 to the LD light amount setting part 501*j* (FIG. 6). As a result, the LD drive circuit 501*h* (FIG. 6) is controlled so as to output a drive current to set the output of the LD 501*d* at 3.4 mW.

Detailed description of the laser light irradiation will follow later.

In step S43 the controller 81 then supplies the white blood cell measurement sample together with the sheath liquid to the sheath flow cell 503. In step S44 the controller 81 starts the clock. Then the forward scattered light, side scattered light, and side fluorescent light are emitted when the laser light irradiates the white blood cells passing through the interior of the sheath flow cell 503. The side scattered light and side fluorescent light emitted from the white blood cells are received by the PD 512 and the APD 511 (FIG. 4), and respectively converted to analog electrical signals. The electrical signals of the side scattered light and the electrical signals of the side fluorescent light are respectively transmitted through amps 63 and 62 (FIG. 4) to the A/D converter 82 (FIG. 2).

In step S45 the calculation part 83 (FIG. 2) obtains the characteristics parameters of the side scattered light and the side fluorescent light. In step S46 the controller 81 then determines whether or not a predetermined time has elapsed since the clock was started When the controller 81 has determined that the predetermined time has not elapsed since the clock was started, the operation returns to step S45. That is, the operation of step S45 is repeated until the predetermined time has elapsed after the clock was started. On the other hand, when it has been determined that the predetermined time has elapsed since the clock was started in step S46, the laser light irradiation is stopped in step S47. Specifically, the LD light amount setting part 501*j* stops the drive current which is supplied from the LD drive circuit 501*h* to the LD 501*d* when the controller 81 supplies a control signal to the LD light amount setting part 501*j*. Then the supply of the white blood cell measurement sample is stopped in step S48. Thereafter, the sheath flow cell 503 is washed in step S49.

[RET Measurement]

Figure 12:
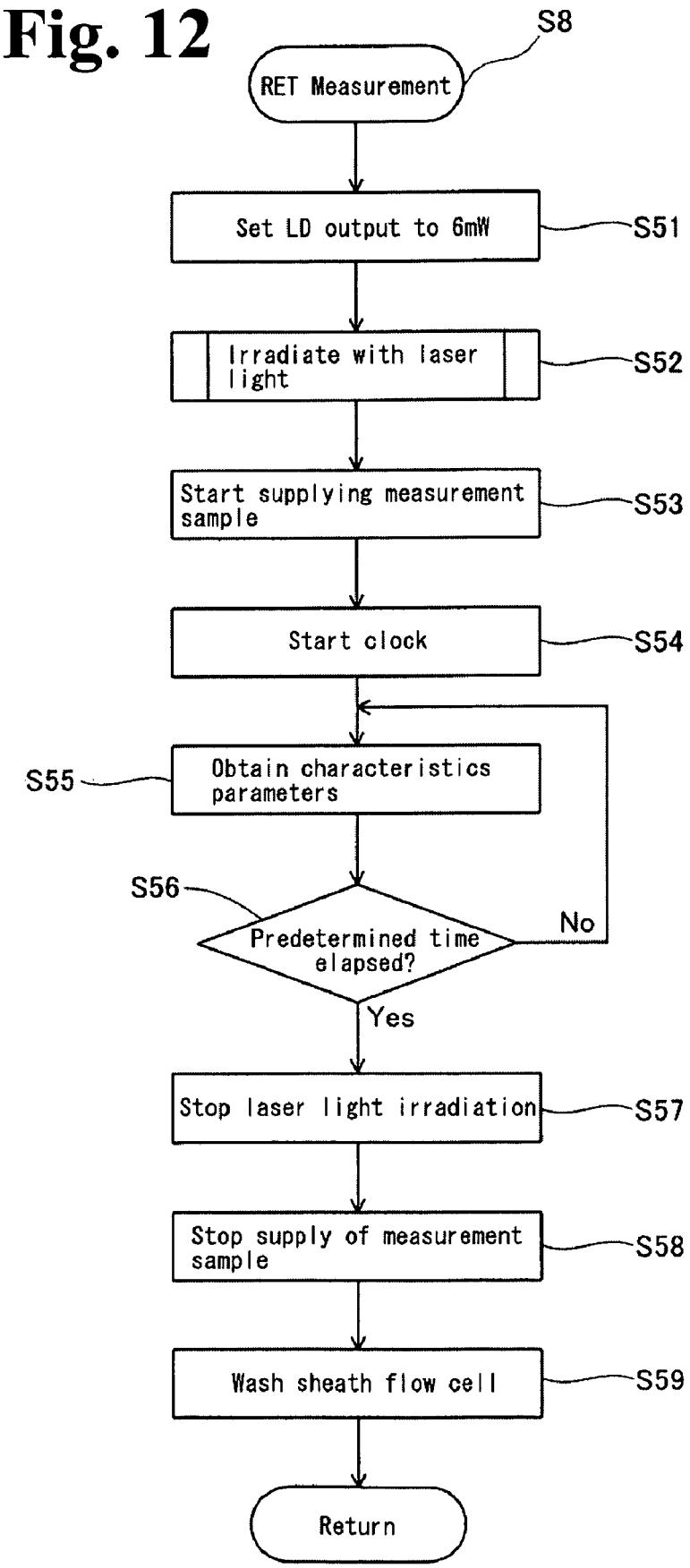
FIG. 12 is a flow chart illustrating the RET measurement operation of the embodiment of the sample analyzer of the present invention.

FIG. 12 is a flow chart illustrating the RET measurement operation of the embodiment of the sample analyzer of the present invention. Details of the RET measurement of step S7 shown in FIG. 7 are described below with reference to FIG. 12 and related drawings.

The controller 81 (FIG. 2) sets the output of the LD 501*d* (FIG. 6) at 6 mW in step S51 in FIG. 12. In step S52 laser light irradiates the sheath flow cell 503 (FIG. 4). Specifically, a control signal is supplied from the controller 81 to the LD light amount setting part 501*j* (FIG. 6). As a result, the LD drive circuit 501*h* (FIG. 6) is controlled so as to output a drive current to set the output of the LD 501*d* at 6 mW.

Detailed description of the laser light irradiation will follow later.

In step S53 the controller 81 then supplies the reticulocyte measurement sample together with the sheath liquid to the sheath flow cell 503. In step S54 the controller 81 starts the clock. Then the forward scattered light, side scattered light, and side fluorescent light are emitted when the laser light irradiates the reticulocytes passing through the interior of the sheath flow cell 503. The forward scattered light and side fluorescent light emitted from the reticulocytes are received by the PD 512 and the APD 511 (FIG. 4), and respectively converted to analog electrical signals. The electrical signals of the forward scattered light and the electrical signals of the side fluorescent light are respectively transmitted through amps 61 and 62 (FIG. 4) to the A/D converter 82 (FIG. 2).

In step S55 the calculation part 83 (FIG. 2) obtains the characteristics parameters of the forward scattered light and the side fluorescent light. In step S56 the controller 81 then determines whether or not a predetermined time has elapsed since the clock was started. When the controller 81 has determined that the predetermined time has not elapsed since the clock was started, the operation returns to step S55. That is, the operation of step S55 is repeated until the predetermined time has elapsed after the clock was started. On the other hand, when it has been determined that the predetermined time has elapsed since the clock was started in step S56, the laser light irradiation is stopped in step S57. Specifically, the LD light amount setting part 501*j* stops the drive current which is supplied from the LD drive circuit 501*h* to the LD 501*d* when the controller 81 supplies a control signal to the LD light amount setting part 501*j*. The supply of the reticulocyte measurement sample is then stopped in step S58. Thereafter, the sheath flow cell 503 is washed in step S59.

[PLT Measurement]

Figure 13:
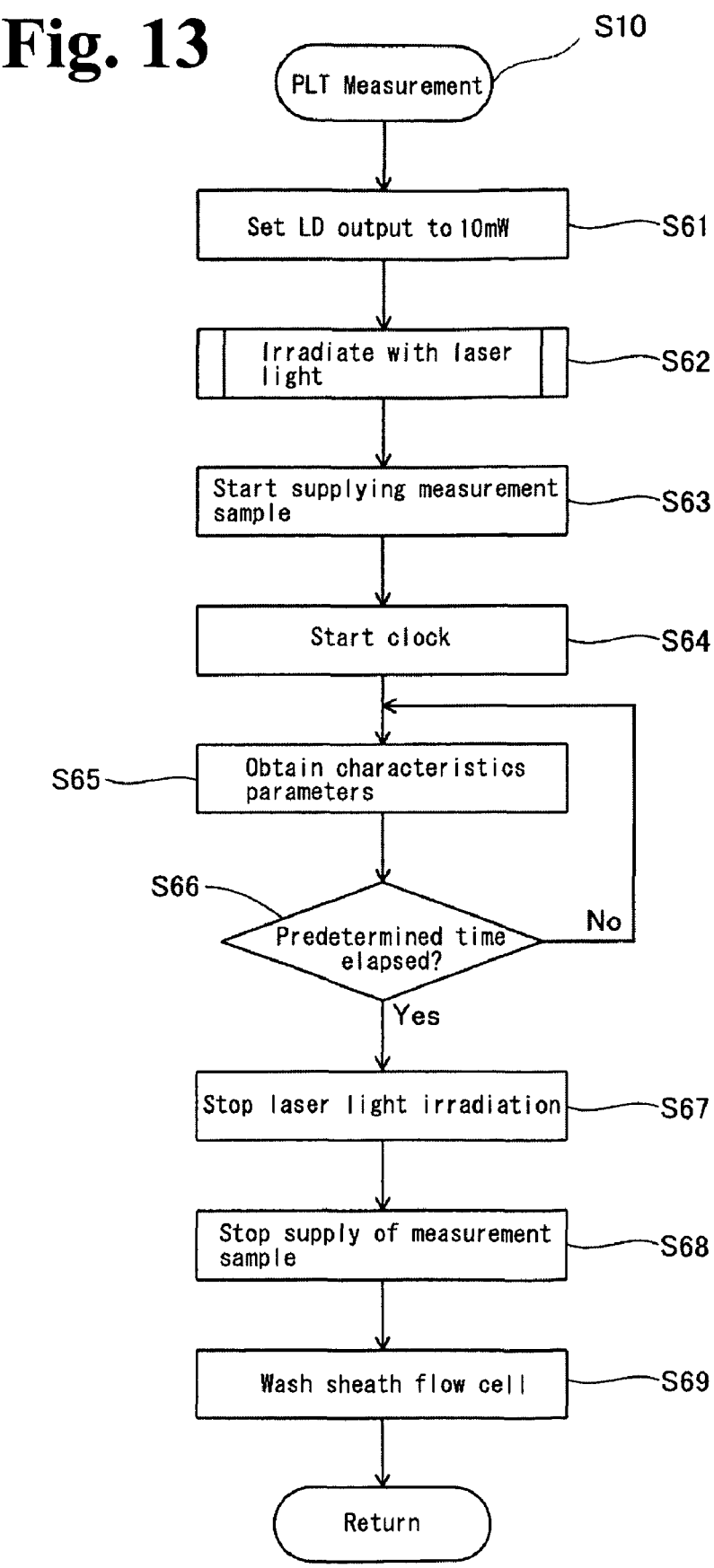
FIG. 13 is a flow chart illustrating the PLT measurement operation of the embodiment of the sample analyzer of the present invention.

FIG. 13 is a flow chart illustrating the PLT measurement operation of the embodiment of the sample analyzer of the present invention. Details of the PLT measurement of step S10 shown in FIG. 7 are described below with reference to FIG. 13 and related drawings.

The controller 81 (FIG. 2) sets the output of the LD 501*d* (FIG. 6) at 10 mW in step S61 in FIG. 13. In step S62 laser light irradiates the sheath flow cell 503 (FIG. 4). Specifically, a control signal is supplied from the controller 81 to the LD light amount setting part 501*j* (FIG. 6). As a result, the LD drive circuit 501*h* (FIG. 6) is controlled so as to output a drive current to set the output of the LD 501*d* at 10 mW.

Detailed description of the laser light irradiation will follow later.

In step S63 the controller 81 then supplies the platelet measurement sample together with the sheath liquid to the sheath flow cell 503. In step S64 the controller 81 starts the clock. Then the forward scattered light, side scattered light, and side fluorescent light are emitted when the laser light irradiates the platelets passing through the interior of the sheath flow cell 503. The forward scattered light and side fluorescent light emitted from the platelets are received by the PD 506 and the APD 511 (FIG. 4), and respectively converted to analog electrical signals. The electrical signals of the forward scattered light and the electrical signals of the side fluorescent light are respectively transmitted through amps 61 and 62 (FIG. 4) to the A/D converter 82 (FIG. 2).

In step S65 the calculation part 83 (FIG. 2) obtains the characteristics parameters of the forward scattered light and the side fluorescent light. In step S66 the controller 81 then determines whether or not a predetermined time has elapsed since the clock was started. When the controller 81 has determined that the predetermined time has not elapsed since the clock was started, the operation returns to step S65. That is, the operation of step S65 is repeated until the predetermined time has elapsed after the clock was started. On the other hand, when it has been determined that the predetermined time has elapsed since the clock was started in step S66, the laser light irradiation is stopped in step S67. Specifically, the LD light amount setting part 501*j* stops the drive current which is supplied from the LD drive circuit 501*h* to the LD 501*d* when the controller 81 supplies a control signal to the LD light amount setting part 501*j*. Then the supply of the platelet measurement sample is stopped in step S68. Thereafter, the sheath flow cell 503 is washed in step S69.

[Laser Light Irradiation]

Figure 14:
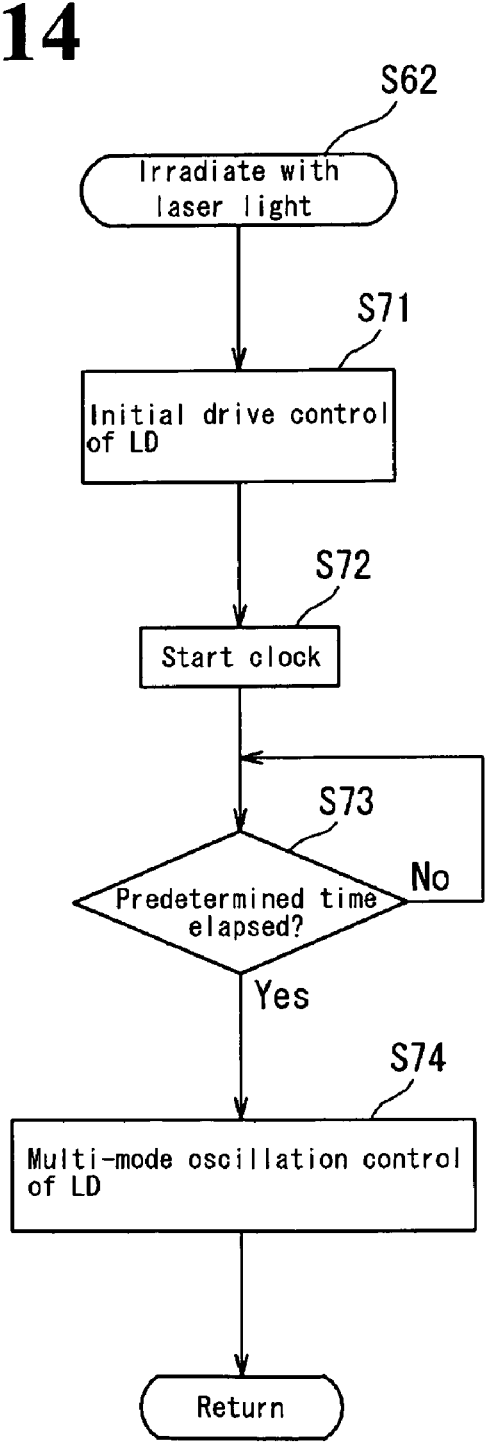
FIG. 14 is a flow chart (subroutine) of laser irradiation performed by the embodiment of the sample analyzer of the present invention.
Figure 16:
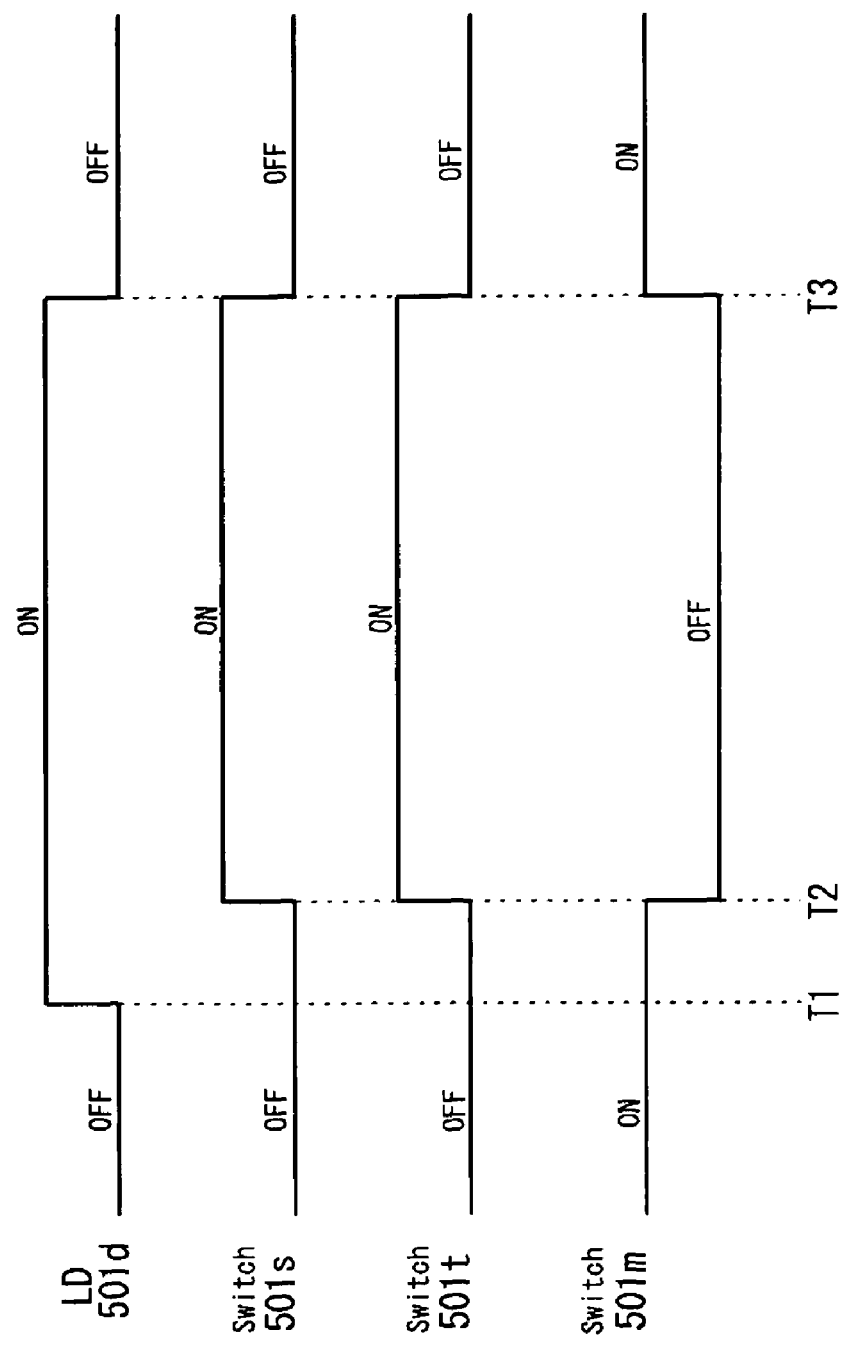
FIG. 16 shows the operation of each switch within the high frequency automatic adjustment circuit and the LD of FIG. 6.

The laser light irradiation performed in the previously mentioned DIFF measurement, RET measurement, and PLT measurement are described in detail below with reference to FIGS. 6, 14, and 16. FIG. 14 is a flow chart (subroutine) related to the laser light irradiation.

In step S71 of FIG. 14 the initial drive control of the LD 501 is performed by starting the laser light irradiation. Specifically, the switches 501*s* and 501*t* are turned off and the switch 501*m* is turned on by instructions from the controller 81, ant at time T1 of FIG. 16 only a predetermined direct current $I_{DC}$ is supplied (a direct current without a high frequency current superimposed thereon) to the LD 501*d*. This time the direct current $I_{DC}$ is supplied to the LD 501*d*, and a voltage signal equivalent to the magnitude of the direct current $I_{DC}$ is also supplied to the holding circuit 501*n* through the closed switch 501*m*.

Furthermore, after time T1 the controller 81 starts the measuring the time (step S72), waits for a predetermined time to elapse during which the direct current $I_{DC}$ stabilizes (step S73), and starts the LD multi-mode oscillation control at time T2 when the predetermined time has elapsed (step S74). Specifically, the controller 81 turns on the switches 501*s* and 501*t*, and turns off the switch 501*m*. Turning off the switch 501*m* maintains the voltage signal, which is equivalent to the magnitude of the direct current $I_{DC}$ before the switch was turned off, in the holding circuit 501*n*. Then the product of multiplying the current value equivalent to the held voltage signal by 0.95 in the multiplying circuit is applied to the comparator 501*q* as a standard current value.

On the other hand, a voltage signal, which is equivalent to the magnitude of the direct current IDC output from the LD drive circuit 501*h* after time T2, is applied to the comparator 501*q* through the closed switch 501*t*. The comparator 501*q* compares the standard current value and the magnitude of the current direct current $I_{DC}$, the error amplifier 501*r* amplifies the difference (error), and an output corresponding to the amplified error is applied as a high frequency bias (voltage) to the high frequency oscillation circuit 501*f* through the switch 501*s*. The high frequency oscillation circuit 501*f* generates a high frequency current $I_{AC}$ which has an amplitude that corresponds to the high frequency bias, and this current $I_{AC}$ is superimposed on the direct current $I_{DC}$ and becomes the drive current of the LD 501*d*.

The amplitude of the high frequency current is temporarily small relative to the $I_{DC}$ at this time (refer to (1) in FIG. 15), and when the LD 501*d* is set in the single mode oscillation state, the average amount of light is identical to that prior to the superposition of the high frequency current so that the amount of light is not adjusted by the APC circuit 501*b*. Then the error generation continues in the comparator 501*q*, and the error amplifier 501*r* and the high frequency oscillation circuit 501*f* operate so as to continue to increase the amplitude of the high frequency current. When the minimum value of the drive current is reduced to less than the threshold value $I_{th}$ by the increase of the amplitude, the $I_{DC}$ is reduced by the function of the previously mentioned APC circuit 501*b*. As a result, there is decreasing difference from the standard current, and the high frequency bias applied to the high frequency oscillation circuit 501*f* converges in a direction which does not increase the amplitude of the high frequency current. This control ultimately brings the direct current $I_{DC}$ output from the LD drive circuit 501*h* near the standard current, that is, the direct current $I_{DC}$ approaches 95% of the direct current when the high frequency current was initially superimposed, and the LD 501*d* maintains the multi-mode oscillation state.

Conversely, the $I_{DC}$ is reduced far more than the standard current value by the function of the APC circuit 501*b* when the amplitude of the high frequency current becomes larger than necessary relative to the direct current $I_{DC}$, even while the LD 501*d* is in the multi-mode oscillation state. In this case, the high frequency oscillation circuit 501f is controlled to suppress the amplitude of the high frequency current in order to increase the $I_{DC}$ so as to approach the standard current value. As a result, therefore, the direct current $I_{DC}$ output from the LD drive circuit 5012h approaches the standard current value, that is, approaches 95% of the direct current when the high frequency current was first superimposed, and the LD 501d maintains the multi-mode oscillation state.

The amplitude of the high frequency current is therefore controlled according to the initial direct current $I_{DC}$, and as a result the direct current $I_{DC}$ approaches 95% of the initial value, and the LD 501d reliably maintains the multi-mode oscillation state.

The high frequency oscillation circuit 501f is controlled such that the amplitude of the high frequency current is less than the maximum rating of the LD 501d. The application of a current which exceeds the maximum rating and reduces the service life of the LD 501d is thus prevented. When the laser light irradiation is stopped (time T3 in FIG. 16), the LD 501d is turned off, the switches 501s and 5012t are both turned off and the switch 501m is turned on. When the laser light irradiates again, the same operation is performed and the amplitude of the high frequency current is adjusted to the direct current each time the LD 501d is turned on, so that the LD 501d reliably maintains the multi-mode oscillation state.

Figure 17:
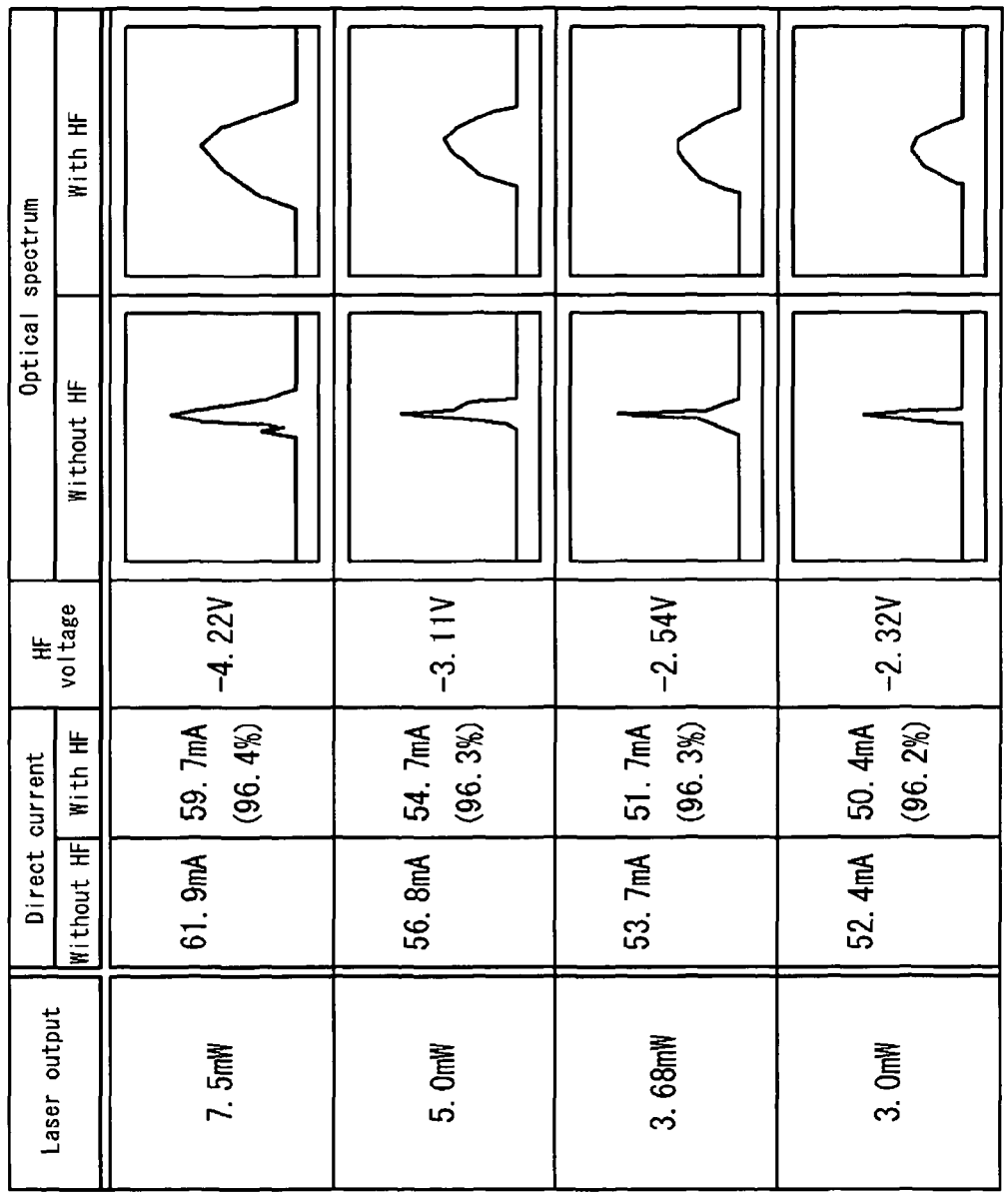
FIG. 17 is a table showing the optical spectrum with and without a high frequency overlay, and the change in the direct current drive current when amplitude control is performed on the high frequency current relative to each type of laser output.

FIG. 17 is a chart showing change in the direction current and the optical spectrum with and without a high frequency superimposed when the amplitude of the high frequency current is controlled relative to each type of laser output as described above. In each type of laser output the direct current is reduced so as to be within a range of 96.2 to 96.4% after the high frequency has been superimposed (with HF) and compared to before the high frequency is superimposed (without HF), so that a value approaching a target of 95% is realized. The optical spectrum pertains to the single mode oscillation state when the high frequency is not superimposed, and pertains to a multi-mode oscillation state which includes a plurality of high frequencies when a high frequency is superimposed.

The amplitude of the high frequency current is controlled according to the direct current output from the APC 501b by controlling the time of laser light irradiation as described above, so that the LD 501d can maintain the multi-mode oscillation state. In such a sample analyzer, therefore, a change is generated in the drive current of the LD 501d by the change over time and the temperature change of the LD 501d, and there is a change in the amount of light according to the change in sample measurement items, and even under these conditions the amplitude of the high frequency current is controlled according to the direct current so that the LD 501d can maintain the multi-mode oscillation state. Even when there has been a change in condition such as a change in the sample measurement item, change over time, and change in temperature, there is no need for manual adjustment in order to maintain the multi-mode since the laser diode can normally maintain the multi-mode oscillation state.

The embodiment described in the present disclosure is an example in all aspects, and should not be construed as limiting the present invention in any way. The scope of the present invention is defined by the scope of the claims and not be the description of the embodiment, and includes all modifications and meanings and equivalences within the scope of the claims.

For example, although an example is described as applying the present invention to a sample analyzer 1 which analyzes blood as a biological sample in the above embodiment, the present invention is not limited to this application inasmuch as the present invention may also be applied to analyzers which measure urine or other component in biological samples.

Although the above embodiment has been described by way of an example in which an input device 303 is provided which has the function of receiving whether or not a DIFF measurement, RET measurement and PLT measurement are set, the present invention is not limited to this arrangement inasmuch as whether or not a DIFF measurement, RET measurement and PLT measurement are set can also be received from a server computer via an electric communication line.

Although the above embodiment offers an example in which a measuring section 2 and a data processing section 3 are provided as respectively separate devices, the present invention is not limited to this arrangement inasmuch as the measuring section and the data processing section may also be provided in a single integrated device.

Although the above embodiment is described in terms of an example in which the high frequency automatic adjustment circuit 501c, an analog circuit, is used as a high frequency current control means, the present invention is not limited to this arrangement inasmuch as the holding circuit 501n and error amplifier 501r may be configured using digital art, and controlling the high frequency current through the CPU.

What is claimed is:

1. A sample analyzer, comprising:
an input device that is used to select a measurement mode corresponding to an analyzed component of a biological sample;
a measurement sample preparation section that comprises at least an aspirating pipette configured to aspirate the biological sample and a chamber configured to receive the biological sample aspirated by the aspirating pipette and a reagent, wherein a measurement sample for analysis under the selected measurement mode is prepared from the biological sample and the reagent received in the chamber;
a flow cell configured to flow the measurement sample therethrough;
a laser diode configured to irradiate the measurement sample flowing through the flow cell with laser light;
a light receiving part configured to receive light from the irradiated measurement sample and to generate electrical signals;
a signal processing circuitry configured to process the electrical signals generated by the light receiving part;
an analysis section configured to analyze the component of the biological sample based on an output from the signal processing circuitry in such a manner peculiar to the selected measurement mode;
a light amount detector configured to detect an amount of light emitted from the laser diode; a direct current output part for configured to output a direct current to be supplied to the laser diode;
a light amount setting part for changing the amount of light emitted from the laser diode according to an analyzed component of the sample by changing the magnitude of the direct current output from the direct current output part, wherein the direct current output part outputs the direct current to be supplied to the laser diode such that the amount of light emitted from the laser diode is maintained at the amount changed by the light amount setting part, based on the amount of light detected by the light amount detector;
a high frequency superimposing part configured to superimpose a high frequency component on the direct current output from the direct current output part; and a high frequency control part configured to control amplitude of the high frequency component output from the high frequency superimposing part according to the magnitude of the direct current output from the direct current output part such that the laser diode oscillates in a multi-mode.

2. The sample analyzer of claim 1, wherein
the high frequency control part controls the high frequency superimposing part such that the laser light output by the laser diode is alternately and repeatedly turned on and off.

3. The sample analyzer of claim 1, wherein
the high frequency control part controls the high frequency superimposing part such that the laser diode oscillates in the multi-mode and a current supplied to the laser diode is less than maximum rating of the laser diode.

4. The sample analyzer of claim 1, wherein
the direct current output part comprises:
a direct current drive circuit configured to supply a direct current to the laser diode; and
a comparator configured to apply an output to the direct current drive circuit according to a difference between the amount of light determined by the controller and the amount of light detected by the light amount detector.

5. The sample analyzer of claim 1, wherein,
the biological sample comprises a blood sample; and
the measurement mode is selected from a blood cell classification measurement mode, a reticulocyte measurement mode or a platelet measurement mode.

6. The sample analyzer of claim 5, wherein:
the analysis section classifies blood cells in the blood sample into a plurality of types of blood cells based on the output from the signal processing circuitry.

7. A sample analyzer comprising:
a laser diode for irradiating a sample with laser light;
a light amount detector for detecting an amount of light emitted from the laser diode;
a direct current output part for outputting a direct current to be supplied to the laser diode such that the amount of light emitted from the laser diode is maintained at a predetermined amount, based on the amount of light detected by the light amount detector
a high frequency superimposing part for superimposing a high frequency component on the direct current output from the direct current output part; and
a high frequency control part for controlling amplitude of the high frequency component output from the high frequency superimposing part according to magnitude of the direct current output from the direct current output part such that the laser diode oscillates in a multi-mode, wherein
the high frequency control part executes an initial drive control for controlling the high frequency superimposing part so as not to superimpose the high frequency component on the direct current output from the direct current output part, and thereafter executes a multi-mode oscillation control for controlling the high frequency superimposing part so as to superimpose the high frequency component on the direct current output from the direct current output part such that the laser diode oscillates in the multi-mode; and
the high frequency control part determines a standard current value based on current value of the direct current output from the direct current output part while executing the initial drive control, and controls the high frequency superimposing part such that the current value of the direct current output from the direct current output part approaches the standard value while executing the multi-mode oscillation control.

8. The sample analyzer of claim 7, further comprising
a light amount setting part coupled to a controller for changing the amount of light emitted from the laser diode according to an analyzed component of the sample by changing the magnitude of the direct current output from the direct current output part;
wherein
the direct current output part outputs the direct current to be supplied to the laser diode such that the amount of light emitted from the laser diode is maintained at the amount of light changed by the light amount setting part.

9. The sample analyzer of claim 7, wherein
the high frequency control part controls the high frequency superimposing part, such that the current value of the direct current to be output from the direct current output part while executing the multi-mode oscillation control has a predetermined relationship with the current value of the direct current output from the direct current output part while executing the initial drive control.

10. The sample analyzer of claim 7, further comprising
a current value information holding part for holding current value information indicating the current value of the direct current output from the direct current output part while executing the initial drive control,
wherein
the high frequency control part determines the standard current value based on the current value information held by the current value information holding part.

11. The sample analyzer of claim 7, wherein
the high frequency control part comprises:
a first circuit for holding current value information indicating the current value of the direct current output from the direct current output part while executing the initial drive control;
a second circuit for determining the standard current value based on the current value information held by the first circuit; and
a comparator for comparing the standard current value and current value information indicating the current value of the direct current output from the direct current output part while executing the multi-mode oscillation control, and a bias voltage according to a comparison result of the comparator is applied to the high frequency superimposing part.

12. A sample analyzing method for analyzing a sample by irradiating a biological sample with laser light from a laser diode using a current on which high frequency component is superimposed, comprising:
monitoring an amount of light emitted from the laser diode;
controlling a magnitude of a direct current to be supplied to the laser diode such that the amount of light emitted from the laser diode is maintained at a predetermined amount, based on the amount of light monitored in the monitoring step; and
controlling amplitude of the high frequency component superimposed on the direct current according to the magnitude of the direct current supplied to the laser diode in the magnitude controlling step such that the laser diode oscillates in a multi-mode,
wherein the amplitude controlling step comprises:
a first step for supplying the direct current to the laser diode without superimposing the high frequency component on the direct current;

a second step for determining a standard current value based on a current value of the direct current supplied to the laser diode in the first step; and a third step for supplying the direct current, on which the high frequency component is superimposed, to the laser diode, and controlling the amplitude of the high frequency component to be superimposed on the direct current such that current value of the direct current, on which the high frequency component is superimposed, approaches the standard value.

13. The method of claim 12, wherein
the amplitude controlling step comprises a step for controlling the amplitude of the high frequency component superimposed on the direct current such that the laser light output by the laser diode is alternately and repeatedly turned on and off.

14. The method of claim 12, further comprising
changing the amount of light emitted from the laser diode according to an analyzed component of the sample by changing the magnitude of the direct current to be supplied to the laser diode,
wherein
the magnitude controlling step comprises a step for controlling the magnitude of the direct current to be supplied to the laser diode such that the amount of light emitted from the laser diode is maintained at the amount of light changed in the light amount changing step.

15. The method of claim 12, wherein
the amplitude controlling step comprises a step for controlling the amplitude of the high frequency component superimposed on the direct current such that the laser diode oscillates in the multi-mode and a current supplied to the laser diode is less than maximum rating of the laser diode.

16. The method of claim 12, wherein
the third step comprises a step for controlling the amplitude of the high frequency component to be superimposed on the direct current such that the current value of the direct current to be supplied to the laser diode in the third step has a predetermined relationship with the current value of the direct current supplied to the laser diode in the first step.

17. The method of claim 12, wherein
the biological sample comprises a blood sample, and
the method further comprises classifying blood cells in the blood sample into a plurality of types of blood cells based on the light from the blood sample irradiated with the laser light.

* * * * *